United States Patent [19]

Yamagishi et al.

[11] Patent Number: 4,954,523

[45] Date of Patent: Sep. 4, 1990

[54] BENZOPHENONE OXIME ETHER COMPOUNDS, PHARMACEUTICAL COMPOSITIONS AND TREATMENT METHODS

[75] Inventors: Youji Yamagishi, Kamiinayoshi; Kozo Akasaka; Takeshi Suzuki, both of Ushiku; Mitsuaki Miyamoto, Ibaraki; Kouji Nakamoto, Tsuchiura; Kazuo Okano, Yatabemachi; Shinya Abe; Hironori Ikuta, both of Ushiku; Kenji Hayashi; Hiroyuki Yoshimura, both of Yatabemachi; Tohru Fujimori, Toyosato; Koukichi Harada, Yatabemachi; Isao Yamatsu, Ushiku, all of Japan

[73] Assignee: Eisai Co., Ltd., Tokyo, Japan

[21] Appl. No.: 364,712

[22] Filed: Jun. 9, 1989

Related U.S. Application Data

[62] Division of Ser. No. 24,737, Mar. 11, 1987, Pat. No. 4,886,834.

[30] Foreign Application Priority Data

Mar. 17, 1986 [JP] Japan ................. 61-57061
Mar. 26, 1986 [JP] Japan ................. 61-65963

[51] Int. Cl.$^5$ ............... A61K 31/15; A61K 31/44; A61K 31/385; A61K 31/40; A61K 31/415; C07C 251/56; C07C 251/50; C07C 213/56

[52] U.S. Cl. .................... 514/521; 514/514; 514/523; 514/539; 514/564; 514/567; 514/640; 514/357; 514/381; 514/383; 514/427; 514/428; 514/440; 558/14; 558/391; 560/35; 562/440; 564/256; 549/39; 546/338; 548/252; 548/561; 548/569; 548/263.6

[58] Field of Search .................. 558/14, 391; 560/35; 562/440; 564/256; 514/514, 523, 539, 564, 567, 640, 521

[56] References Cited

PUBLICATIONS

Mixich et al., Chem. Abstracts, vol. 93, 15; 149994e, (1980).
Yamagishi et al., Chem. Abstracts, vol. 109, 9; 73155h, (1988).
Waring et al., Chem. Abstracts, vol. 90, 3; 22599n, (1979).
Seperic, Chem. Abstracts, vol. 85, 25; 192456c, (1976).
Zagorenskii et al., Chem. Abstracts, vol. 72, 1; 3316e, (1970).
Akasaka et al., Chem. Abstracts, vol. 106, 15; 119453x, (1987).
Macchia et al., Chem. Abstracts, vol. 105, 9; 78524e, (1986).

*Primary Examiner*—John M. Ford
*Assistant Examiner*—J. Richter
*Attorney, Agent, or Firm*—Flynn, Thiel, Boutell & Tanis

[57] ABSTRACT

A new diphenyl-methane derivative is useful to inhibit agglomeration of blood and is defined by the formula, including a diphenylethylene derivative and a benzophenone oxime ether derivative.

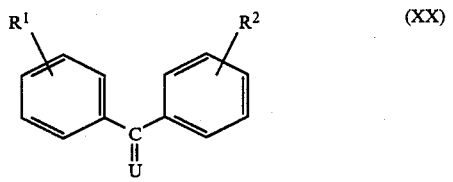

in which $R^1$ and $R^2$ each are hydrogen, hydroxyl or a lower alkoxy, U is =CXY or =N—O—W, X is hydrogen, cyano or —COR6, R6 being hydroxyl or an amino, Y is —R10—COOR3, R3 being hydrogen or a lower alkoxy, R10 being an alkylene having 1 to 3 carbon atoms, straight or branched, —CO—NR4R5, R4 and R5 each being hydrogen, a lower alkyl or a lower aralalkyl, —CH2—NH-SO3—C6H5 or —C(R8)=NR7, R7 being a lower alkoxy or an aryl, R8 is —VR9, V being oxygen, sulfur or nitrogen, R9 being an alkyl or an aryl, W is —CH2—CO—CH2—COOR13, R13 being hydrogen or a lower alkyl, —CH2—C(=NOR14)—CH2—COOR15, R15 being hydrogen or a lower alkyl, R14 being a lower alkyl, —CH(CN)—(CH2)$q$—COOR16, R16 being hydrogen or a lower alkyl, q being an integer of 1 to 3, or —(CH2)p—Z, Z being —SH, —SCN or a monovalent group derived from a five- or six-membered ring which may be substituted by a ring having one or more sulfur atoms in the ring, p being 1 or 2.

19 Claims, No Drawings

BENZOPHENONE OXIME ETHER COMPOUNDS, PHARMACEUTICAL COMPOSITIONS AND TREATMENT METHODS

This is a division of application Ser. No. 07/024,737 filed 3-11-87, now Pat. No. 4,886,834.

The invention relates to a diphenyl-methane derivative, a process for preparing the same and the pharmaceutical use thereof. In particular, it relates to a diphenylethylene derivative and a benzophenone oxime ether derivative.

The most serious diseases for mankind at present include acute vascular diseases such as myocardial infarction, cerebral, apoplexy, cerebral thrombosis, cerebral infarction, pulmonary embolus, deep phlebothrombosis and peripheral arteriothrombosis.

Recently antiplatlet agents have attracted public attention and been clinically employed for treating these diseases. However their application has been only lately realized. Thus it is expected to develop better drugs in future.

The invention provides a diphenyl-methane derivative having the formula (XX) and a pharmacologically acceptable salt thereof:

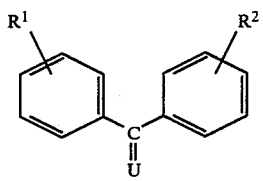

in which $R^1$ and $R^2$ each are hydrogen, hydroxyl or a lower alkoxy, U is $=CXY$ or $=N-O-W$, X is hydrogen, cyano or —COR6, $R^6$ being hydroxyl or amino, Y is —$R^{10}$-COOR$^3$, $R^3$ being hydrogen or a lower alkyl, $R^{10}$ being an alkylene having 1 to 3 carbon atoms, straight or branched, —CO—NR$^4$R$^5$, $R^4$ and $R^5$ each being hydrogen, a lower alkyl or a lower arylalkyl, —CH2—NHSO2-NHSO2-C6H5 or —C($R^8$)=NR$^7$, $R^7$ being a lower alkoxy or an aryl, $R^8$ is —VR$^9$, V being oxygen, sulfur or nitrogen, $R^9$ being an alkyl or an aryl, W is —CH2—CO—CH2-COOR$^{13}$, $R^{13}$ being hydrogen or a lower alkyl, —CH2—C(=NOR$^{14}$)—CH2—COOR$^{15}$, $R^{15}$ being hydrogen or a lower alkyl, $R^{14}$ being a lower alkyl, —CH(CN)—(CH2)$q$—COOR$^{16}$, $R^{16}$ being hydrogen or a lower alkyl, q being an integer of 1 to 3, or —(CH2)$p$—Z, Z being —SH, —SCN or a monovalent group derived from a five- or six-membered ring which may be substituted by a ring having one or more sulfur atoms in the ring, p being 1 or 2.

In the formula (XX), $R^{10}$ may be defined by —(CH2)$n$— in which n is 1, 2 or 3.

The diphenyl-methane derivative as defined above includes two embodiments. One is a diphenylmethane derivative having the formula (XX) in which U is $=CXY$, also called a diphenylethylene derivative. The other is a diphenyl-methane having the formula (XX) in which U is $=N-O-W$, called a benzophenone oxime ether derivative. The invention will be explained in detail below in view of these two embodiments.

In addition, the invention provides a plurality of processes for preparing the above defined diphenylmethane derivative. Each process is explained below in detail.

Moreover the invention provides a pharmaceutical composition which comprises a pharmacologically effective amount of the diphenyl-methane derivative as defined above or a pharmacologically acceptable salt thereof and a pharmacologically acceptable carrier.

In this connection, the invention provides a method for treating a disease caused by the blood stream disorder with administration of the diphenylmethane derivative as defined above or a pharmacologically acceptable salt thereof.

The invention compound will be explained in more detail in line with the above shown embodiments.

In one aspect of the invention, the desired compound of the present invention is a substituted diphenylethylene derivative of the general formula (I) or a pharmaceutically acceptable salt thereof:

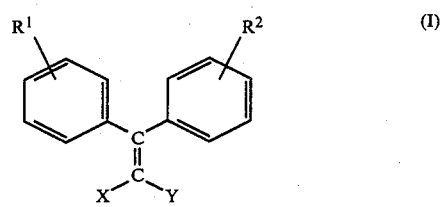

wherein $R^1$ and $R^2$ may be the same or different from each other and each represents a hydrogen atom, hydroxyl or a lower alkoxy group; X represents a hydrogen atom, COR$^6$ or a cyano group wherein $R^6$ is hydroxyl or amino; and Y represents a group of the formula —(CH2)$_n$—COOR$^3$ (wherein $R^3$ represents a hydrogen atom or a lower alkyl group; and n is an integer of 1 to 3), a group of the formula

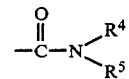

(wherein $R^4$ and $R^5$ may be the same or different from each and each represents a hydrogen atom or a lower alkyl or arylalkyl group) or a group of the formula

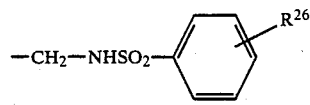

(wherein $R^{26}$ represents a hydrogen atom or a lower alkyl group), Y may be further C($R^8$)=NR$^7$.

In the above definition, a lower alkyl group as mentioned with regard to $R^3$, $R^4$ and $R^5$ includes straight-chain or branched alkyl groups carrying one to six carbon atoms, e.g., methyl, ethyl, n-propyl, n-butyl, isopropyl, isobutyl, 1-methylpropyl, tert-butyl, n-pentyl, 1-ethylpropyl, isoamyl and n-hexyl groups. An alkoxy group as mentioned with regard to $R^1$ and $R^2$ includes any lower alkoxy group derived from the lower alkyl groups as cited above. Among these groups, methyl and ethyl groups are the most desirable lower alkyl groups while a methoxy group is the most desirable lower alkoxy group.

An arylalkyl group as mentioned with regard to $R^4$ and $R^5$ includes benzyl, 2-chlorobenzyl, 3-chlorobenzyl, 4-chlorobenzyl, 2-methylbenzyl, 3-methylbenzyl, 4-methylbenzyl, 2-methoxybenzyl, 3-methoxybenzyl, 4-methoxybenzyl and phenethyl groups as well as heteroaryl groups such as 2-picolyl, 3-picolyl and 4-picolyl groups.

A pharmaceutically acceptable salt of the aimed compound wherein $R^3$ is a hydrogen atom includes metals salts such as Na, K, Ca and Mg salts.

Process for Preparation

There may be various processes for preparing the compound (I) of the present invention. Typical examples thereof are as follows.

(1) The aimed compound of the formula (I), wherein Y is a group of the formula

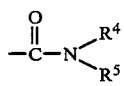

(wherein $R^4$ and $R^5$ may be the same or different from each other and each represents a hydrogen atom or a lower alkyl or arylalkyl group).

A carboxylic acid of the general formula (II):

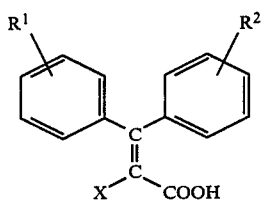

wherein $R^1$, $R^2$ and X are as defined above, or a reactive acid derivative thereof is converted into an amide by reacting with an amine of the general formula:

wherein $R^4$ and $R^5$ are as defined above, to give a compound (I') which is one of the aimed compounds of the present invention:

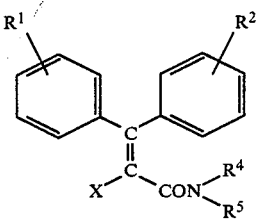

wherein $R^1$, $R^2$, X, $R^4$ and $R^5$ are as defined above.

A reactive acid derivative of the compound (III) includes, for example, a halide, an anhydride or a mixture of acid anhydrides of the compound (III). This reaction may be carried out in the presence of dehydrating agent(s) such as N,N'=dicyclohexylcarbodiimide, N,N'-diethylcarbodiimide, trialkyl phosphates, polyphosphate or tosyl chloride, if required.

When a halide is used as a reactive derivative, base(s) may be added to the reaction mixtures to bind the hydrogen halide formed during the reaction, thus accelerating the reaction. Examples of the bases are inorganic salts such as potassium hydroxide, sodium hydroxide, potassium carbonate and sodium carbonate and tertiary amines such as pyridine and triethylamine.

This reaction may be usually carried out in a solvent. Any solvent may be employed so long as it exhibits no adverse effect on the reaction. Examples of such a solvent are dimethyl sulfoxide, tetrahydrofuran, dioxane, ethanol and mixtures thereof.

The reaction may be usually carried out at a temperature of −50° to 200° C. unless particularly limited. After the completion of the reaction, the aimed compound may be isolated in a conventional manner.

(2) The aimed compound of the formula (I), wherein Y is a group of the formula

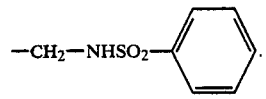

An amine of the general formula (IV):

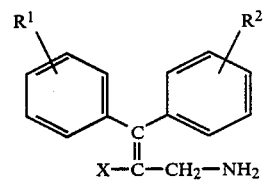

wherein $R^1$, $R^2$ and X are as defined above, is reacted with a sulfonyl halide of the general formula (V):

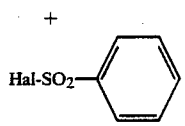

wherein Hal represents a halogen atom, in a conventional manner to thereby readily give the aimed compound (I'') in the form of a sulfonamide:

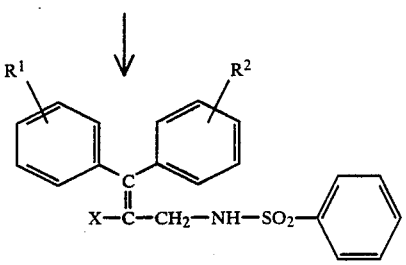

This reaction may be usually carried out in a solvent. Any solvent may be employed so long as it exhibits no adverse effect on the reaction. Examples of such a solvent are chloroform, 1,2-dichloroethane, ethyl ether, pyridine, tetrahydrofuran, dioxane, ethylene glycol dimethyl ether, benzene, toluene and mixtures thereof.

The temperature at which this reaction is carried out is not particularly limited. Usually a temperature of −50° to 150° C. is preferable. After the completion of the reaction, the aimed compound may be isolated in a conventional manner.

(3) The aimed compound of the formula (I), wherein Y is a group of the formula —(CH$_2$)$_n$—COOR$^3$ (wherein n and R$^3$ are as defined above).

A ketone of the general formula (VI):

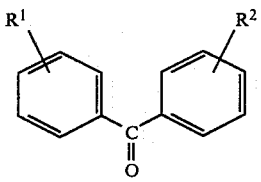

wherein R$^1$ and R$^2$ are as defined above, is reacted with a halide of the general formula (VII):

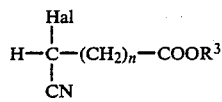

wherein Hal represents a halogen atom; and n and R$^3$ are as defined above, for example, in the presence of zinc in tetrahydrofuran in a conventional manner to give a hydroxy compound of the formula (VIII) (Reformatsky's reaction).

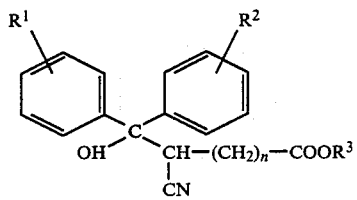

Examples of the solvent available for the above reaction are tetrahydrofuran, benzene and ether. Further a solvent mixture comprising, for example, trimethyl borate or triethyl borate with tetrahydrofuran may be employed.

This reaction may be usually carried out at a temperature of approximately −70° to 150° C.

The hydroxy compound (VIII) thus obtained may be dehydrated in a conventional manner to give a compound (I''') which is one of the aimed compounds of the present invention.

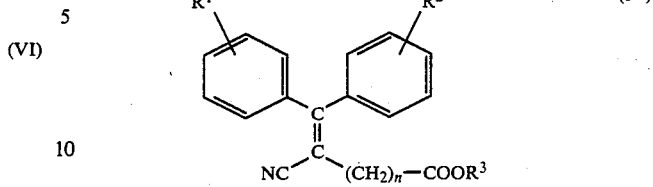

Examples of the solvent available for this reaction are benzene, toluene, tetrahydrofuran, ether and dioxane, while examples of the catalyst therefor are p-toluenesulfonic acid, thionyl chloride phosphorus pentaoxide, iodine and hydrochloric acid. This reaction may be carried out at a temperature of approximately −70° to 150° C.

The invention compound is defined to include a compound having the formula (I) in which Y is —C(R$^8$)=NR$^7$, that is, —C(VR$^9$)=NR$^7$, which falls within the scope of the first embodiment. R$^9$ is an alkyl, a substituted alkyl, an alkenyl or an aryl.

The compound is prepared by the below given procedures.

(7) A compound having the formula (I) in which Y is —CONHR$^7$ is reacted with a compound having the formula of HVR$^9$ by a halogenating agent such as phosphorus oxychloride, phosphorus pentachloride and thionyl chloride to obtain a compound having the formula (I) in which Y is —C(VR$^9$)=NR$^7$, in a solvent such as benzene, toluene and chloroform. The reaction may be effected in the presence of an organic base such as dimethylaniline, triethylamine and pyridine or an inorganic base such as potassium carbonate and sodium carbonate.

(8) The same starting compound as used in the preparation (7) is reacted with a sulfurizing agent such as phosphorus pentasulfide in a solvent such as benzene and toluene to obtain a corresponding thioamide having the formula (I) in which Y is —C(=S)—NH—R$^7$. Then the thioamide is reacted with a halide having the formula of R$^9$-hal to obtain a compound having the formula (I) in which Y is —C(SR$^9$)=NR$^7$. A solvent and a base may be used in the same way as shown in the preparation (7).

(9) A compound having the formula (I) in which Y is —C(VR$^9$)=NR$^7$, R$^9$ is an alkyl or a substituted alkyl and R$^7$ is a lower alkoxy is obtained below. A compound having the formula (I) in which Y is —CO—VR$^9$ is reacted with H2N-R$^7$ to obtain the above intended compound.

The above shown procedures are illustrated below.

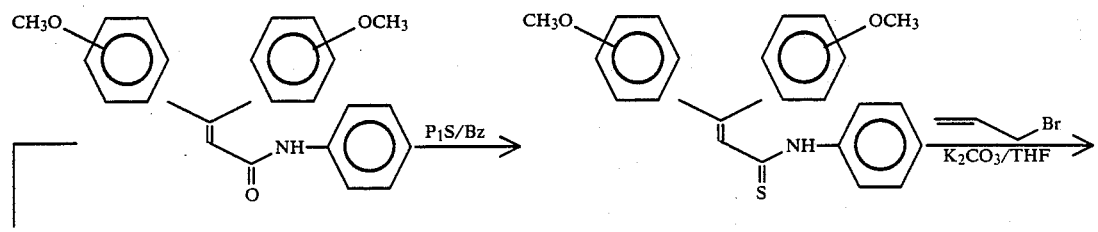

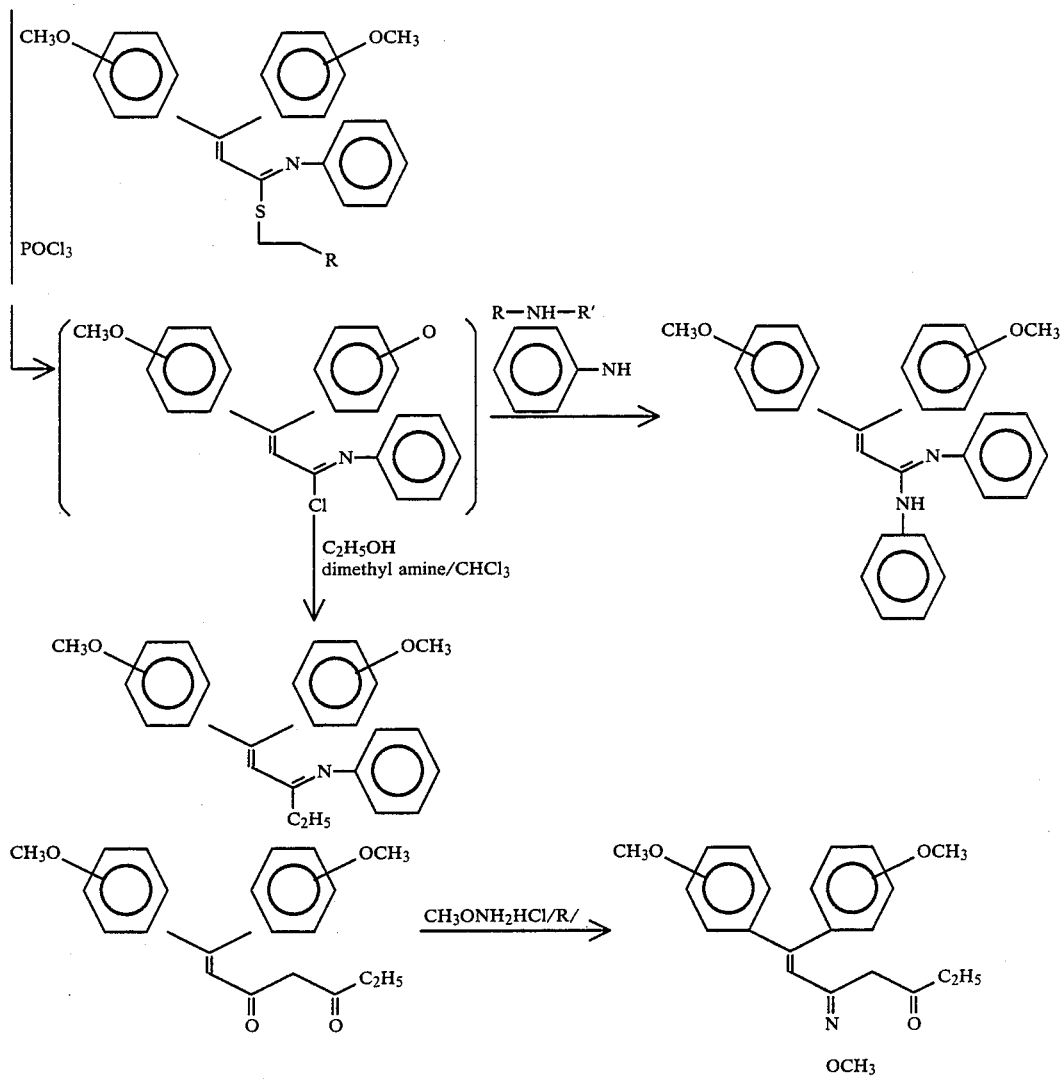

In order to further illustrate the present invention, and not by way of limitation, typical examples of the compound of the present invention will be given. Each compound will be shown in free form.

N-benzyl-3,3-bis(4-methoxyphenyl)acrylamide,
N-(2-chlorobenzyl)-3,3-bis(4-methoxyphenyl)acrylamide,
N-(3-chlorobenzyl)-3,3-bis(4-methoxyphenyl)acrylamide,
N-(4-chlorobenzyl)-3,3-bis(4-methoxyphenyl)acrylamide,
N-(2-methylbenzyl)-3,3-bis(4-methoxyphenyl)acrylamide,
N-(3-methylbenzyl)-3,3-bis(4-methoxyphenyl)acrylamide,
N-(4-methylbenzyl)-3,3-bis(4-methoxyphenyl)acrylamide,
N-(2-methoxyphenyl)-3,3-bis(4-methoxyphenyl)acrylamide,
N-(3-methoxybenzyl)-3,3-bis(4-methoxyphenyl)acrylamide,
N-(4-methoxybenzyl)-3,3-bis(4-methoxyphenyl)acrylamide,
N-(2-picolyl)-3,3-bis(4-methoxyphenyl)acrylamide,
N-(3-picolyl)-3,3-bis(4-methoxyphenyl)acrylamide,
N-(4-picolyl)-3,3-bis(4-methoxypehnyl)acrylamide,
N-[3,3-bis(4-methoxyphenyl)allyl]benzenesulfonamide,
N-[3,3-bis(4-methoxyphenyl)allyl]-p-toluenesulfonamide,
ethyl 4-cyano-5,5-bis(4-methoxyphenyl)-4-pentenoate,
4-cyano-5,5-bis(4-methoxyphenyl)-4-pentenoic acid,
methyl 5-cyano-6,6-bis(4-methoxyphenyl)-5-hexenoate,
ethyl 3-cyano-4,4-bis(4-methoxyphenyl)-3-butenoate,
ethyl 4-cyano-5,5-bis(4-ethoxyphenyl)-4-pentenoate,
methyl 4-cyano-5,5-bis(4-ethoxyphenyl)-4-pentenoate,
4-cyano-5,5-bis(4-ethoxyphenyl)-4-pentenoic acid,
5-cyano-6,6-bis(4-ethoxyphenyl)-5-hexenoic acid, and
3-cyano-4,4-bis(4-ethoxyphenyl)-3-butenoic acid.

In addition to this compound species and the compounds obtained in Examples about the first embodiment of the invention, the following compounds are included within the scope of the invention.

N-phenyl-3,3-bis(4-methoxyphenyl)acrylamide in which the phenyl may be substituted at 2, 3 or 4 position by chlorine.

N-(2-, 3- or 4-pyridyl)-3,3-bis(4-methoxyphenyl)acrylamide

N-(2-, 3- or 4-pyridyl)methyl-3,3-bis(4-methoxyphenyl)acrylamide
N-phenyl-N-methyl or isopropyl-3,3-bis(4-methoxyphenyl)acrylamide
N-(2-, 3- or 4-pyridyl)-N-methyl-3,3-bis(4-methoxyphenyl)acrylamide
N-(2-, 3- or 4-pyridyl)-N-isopropyl-3,3-bis(4-methoxyphenyl)acrylamide
N-(2-(N,N-dialkylamino)ethyl-3,3-bis(4-methoxyphenyl)acrylamide, the alkyl being methyl or ethyl.
N-(3-(N,N-dialkylamino)propyl-3,3-bis(4-methoxyphenyl)acrylamide, the alkyl being methyl or ethyl.
N,N-bis(2-(N,N-dimethylamino)ethyl)-3,3-bis(4-methoxyphenyl)acrylamide
N-(2-(N,N-dimethylamino)ethyl)-N-benzyl-3,3-bis(4-methoxyphenyl)acrylamide
N-phenyl-3,3-bis(4-ethoxyphenyl)acrylamide in which the phenyl may be replaced by 2-chlorophenyl, 3-pyridyl, benzyl, 2-chlorobenzyl or (3-pyridyl)methyl.
N-phenyl-N-methyl-3,3-bis(4-ethoxyphenyl)acrylamide in which the phenyl may be replaced by 3-pyridyl or benzyl.
N-benzyl-N-isopropyl-3,3-bis(4-ethoxyphenyl)acrylamide
N-(2-(N,N-dimethylamino)ethyl)-3,3-bis(4-ethoxyphenyl)acrylamide
N-(2-(N,N-diethylamino))ethyl)-N-(2-(3,4-dimethoxyphenyl)ethyl)-3,3-bis(4-ethoxyphenyl)acrylamide
N-benzyl-3,3-bis(4-hydroxyphenyl)acrylic amide
N-benzyl-3-(4-methoxyphenyl)-3-(4-ethoxyphenyl)acrylic amide
N-benzyl-N-methyl-3-(4-methoxyphenyl)-3-(4-ethoxyphenyl)acrylic amide
N-(2-(N,N-dimethylamino)ethyl)-N-(2-(3,4-dimethoxyphenyl)ethyl)-3-(4-methoxyphenyl)-3-(4-ethoxyphenyl)acrylic amide
3,3-bis(4-methoxy, 4-ethoxy or 4-hydroxyphenyl)-N-phenyl-acrylic imino acid ethyl ester
3-(4-methoxyphenyl)-3-(4-ethoxyphenyl)-N-phenylacrylic imino acid ethyl ester
3,3-bis(4-methoxyphenyl)-N-benzyl-acrylic imino acid ethyl ester
3,3-bis(4-methoxyphenyl)-N-(3-pyridyl)-acrylic imino acid methyl ester
3,3-bis(4-methoxy-, 4-ethoxy- or 4-hydroxy-phenyl)-N,N'-diphenylacrylic amidine
3-(4-methoxyphenyl)-3-(4-ethoxyphenyl)-N,N'-diphenylacrylic amidine
3,3-bis(4-methoxy- or 4-ethoxy-phenyl)-N,N'-dienzylacrylic amidine
3,3-bis(4-methoxyphenyl)-N-phenyl-N'-benzylacrylic amidine
3,3-bis(4-methoxy-, 4-ethoxy- or 4-hydroxy-phenyl)-N-phenyl-acrylic thioimino acid allyl ester
3-(4-methoxyphenyl)-3-(4-ethoxyphenyl)-N-phenylacrylic thioimino acid allyl ester
3,3-bis(4-methoxyphenyl)-N-benzyl-acrylic thioimino acid allyl ester
3,3-bis(4-methoxyphenyl)-N-(3-pyridyl)-acrylic thioimino acid ethyl ester
methyl 3-methoxyimino-5,5-bis(4-ethoxyphenyl)-4-penenoate
3-methoxyimino-5,5-bis(4-methoxy- or 4-ethoxyphenyl)-4-pentenoic acid
3-methoxyimino-5-(4-methoxyphenyl)-5-(4-ethoxyphenyl)-4pentenoic acid
N-(3,3-bis(4- ethoxy- or 4-hydroxy-phenyl)allyl)-methanesulfonic amide
N-(3-(4-methoxyphenyl)-3-(4-ethoxyphenyl)allyl)-methanesulfonic amide
N-(3,3-bis(4ethoxy- or 4-hydroxyphenyl)allyl)-benzenesulfonic amide
N-(3-(4-methoxyphenyl)-3-(4-ethoxyphenyl)allyl)-benzenesulfonic amide
N-(3,3-bis(4-ethoxy- or 4-hydroxy-phenyl)allyl)-beta-toluenesulfonic amide
N-(3-(4-methoxyphenyl)-3-(4-ethoxyphenyl)allyl)-beta-toluenesulfonic amide
N-(3,3-bis(4-ethoxy- or 4-hydroxy-phenyl)allyl)-4-carboxybenzenesulfonic amide
N-(3-(4-methoxyphenyl)-3-(4-ethoxyphenyl)allyl)-4-carboxybenzenesulfonic amide
ethyl 3- cyano-4,4-bis(4-ethoxy- or 4-hydroxy-phenyl)-3-butenoate
ethyl 3-cyano-4-(4-methoxyphenyl)-4-(4-ethoxyphenyl)-3-butenoate
3-cyano-4,4-bis(4-methoxyphenyl)-3-butenoic acid
3-cyano-4,4-bis(4-hydroxyphenyl)-3-butenoic acid
3-cyano-4-(4-methoxyphenyl)-4-(4-ethoxyphenyl)-3-butenoic acid
ethyl 4-cyano-5,5-bis(4-methoxyphenyl)-4-pentenoate
ethyl 4-cyano-5,5-bis(4-hydroxyphenyl)-4-pentenoate
ethyl 4-cyano-5-(4-methoxyphenyl5-(4-ethoxyphenyl)-4-pentenoate
ethyl 4-cyano-5-(4-hydroxyphenyl)-(Z)- or (E)-5-(4-methoxyphenyl)-4-pentenoate
ethyl 4-cyano-5-(4-hydroxyphenyl)-(Z)- or -(E)-5-(4-ethoxyphenyl)-4-pentenoate, 4-cyano-5-(4-methoxyphenyl)-5-(4-ethoxyphenyl)-4-pentenoic acid
ethyl 4-cyano-2-methyl-5,5-bis(4-methoxy-, 4-ethoxy- or 4-hydroxy-phenyl)-4-pentenoate
ethyl 4-cyano-2-methyl-5-(4-methoxyphenyl)-5-(4-ethoxyphenyl)-4-pentenoate, 4-cyano-2-methyl-5,5-bis(4-ethoxy- or 4-hydroxy-phenyl)-4-pentenoic acid
4-cyano-2-methyl-5-(4-methoxyphenyl)-5-(4-ethoxyphenyl)-4-pentenoic acid
methyl 5-cyano-6,6-bis(4-ethoxy- or 4-hydroxyphenyl)-5-hexenoate
methyl 5-cyano-6-(4-methoxyphenyl)-6-(4-ethoxyphenyl)-5-hexenoate
5-cyano-6,6-bis(4-methoxy- or 4-hydroxy-phenyl)-5-hexenoic acid
5-cyano-6-(4-methoxyphenyl)-6-(4-ethoxyphenyl)-5-hexenoic acid
ethyl 4-ethoxycarbonyl-5,5-bis(4-methoxyphenyl)-4-pentenoate
4-carboxy-5,5-bis(4-ethoxy- or 4-hydroxy-phenyl)-4-pentenoic acid
4-carboxy-5-(4-methoxyphenyl)-5-(4-ethoxyphenyl)-4-pentenoic acid
ethyl 4-carbamoyl-5,5-bis(4-methoxyphenyl-4-pentenoate
4-carbamoyl-5,5-bis(4-ethoxy- or 4-hydroxy-phenyl)-4-pentenoic acid
4-carbamoyl-5-(4-methoxyphenyl)-5-(4-ethoxyphenyl)-4-pentenoic acid The aimed compound of the present invention is a substituted benzophenone oxime ether derivative of the general formula (I) or a pharmaceutically acceptable salt thereof:

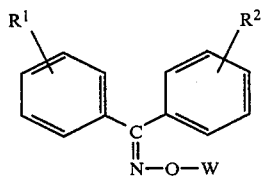 (I)

wherein R¹ and R² may be the same or different from each other and each represents a hydrogen atom or a lower alkoxy group; and W represents a group of the formula

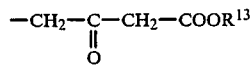

(wherein R¹³ is a hydrogen atom or a lower alkyl group), a group of the formula

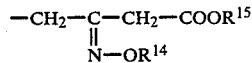

(wherein R¹⁵ represents a hydrogen atom or a lower alkyl group; and R¹⁴ represents a lower alkyl group), a group of the formula

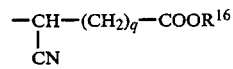

(wherein R¹⁶ represents a hydrogen atom or a lower alkyl group; and q us an integer of 1 to 3) or a group of the formula—(CH₂)$_p$—Z wherein Z represents a group of the formula—SH, a group of the formula—SCN or a monovalent group derived from a five- or six-membered ring optionally substituted by a ring having one or more sulfur atoms in the ring; and p is an integer of 1 to 2).

In the above definition, a lower alkyl group as mentioned with regard to R¹³, R¹⁴, R¹⁵ and R¹⁶ includes straight-chain or branched alkyl groups carrying one to six carbon atoms, e.g., methyl, ethyl, n-propyl, n-butyl, isopropyl, isobutyl, 1-methylpropyl, tert-butyl, n-pentyl, 1-ethylpropyl, isoamyl and n-hexyl groups. An alkoxy group as mentioned with regard to R¹ and R² includes any lower alkoxy group derived from the lower alkyl groups as cited above. Among these groups, methyl and ethyl groups are the most desirable lower alkyl groups while a methoxy group is the most desirable lower alkyl group.

A monovalent group derived from a five- or six-membered ring optionally substituted by a ring containing one or more sulfur atoms in the ring as mentioned with regard to Z of the compound (XI) of the invention includes, for example, 1-pyrrolyl, 1-(1,2,3,4-tetrazolyl), 1-pyrrolidinyl, 1,3-dithianyl and 3-allylmercapto-1,2,4-triazolyl groups.

A pharmaceutically acceptable salt of the aimed compound of the formula (XI) in which R¹³, R¹⁵ and/or R¹⁶ are hydrogen atoms includes metal salts such as Na, K, Ca and Mg salts.

Further some of the aimed compounds can be converted into acid addition salts by reacting the same with a pharmaceutically acceptable inorganic or organic acid. Examples of such inorganic acids are hydrochloric, hydrobromic, hydroiodic and sulfuric acids. Examples of such organic acids are maleic, fumaric, succinic, acetic, malonic, citric, benzoic, oxalic and methane-sulfonic acids.

Process for Preparation

There may be various processes for preparing the compound (XI) of the invention. Typical examples thereof are as follows.

Preparation process 4

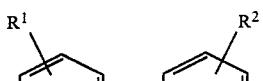 (XII)

[Step 1] 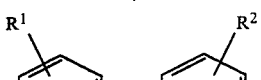 (XIII)

Hal—W (XIV)

[Step 2] 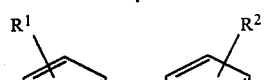 (XI)

wherein R¹, R² and W are defined above; and Hal represents a halogen atom.

Namely, a benzophenone compound of the formula (XII) is reacted with a hydroxylamine to give a benzophenone oxime of the formula (XIII) (Step 1). Then the compound (XIII) is condensed with a halide of the formula (XIV) to give the aimed compound (XV) (Step 2). The obtained product may be converted into a pharmaceutically acceptable salt in a conventional manner, if required.

Step 1 may be usually carried out at a temperature of approximately 0° to 200° C., preferably at room temperature to 100° C. with the use of a solvent such as methanol, ethanol, propanol, benzene, toluene or water.

Step 2 may be usually carried out at a temperature of approximately 0° to 100° C. with the use of a solvent such as dimethylformamide (DMF), dimethyl sulfoxide (DMSO), methanol, ethanol, propanol, benzene or toluene. The reaction may be carried out in the presence of a base such as sodium hydride (NaH), triethylamine, dimethylaniline, potassium hydroxide, methoxysodium (NaOMe), ethoxysodium (NaOEt) or tert-butoxypotassium to give a preferable result.

Preparation process 5

Aimed compound of the formula (XI) wherein R¹³, R¹⁵ and R¹⁶ in W are hydrogen atoms An ester of the formula:

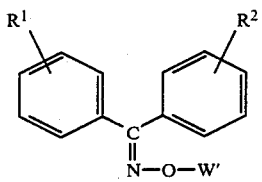

wherein W' has the same meaning as that of W in the general formula (XI) except that $R^{13}$, $R^{15}$, and $R^{16}$ *are hydrogen atoms, i.e., lower alkyl groups, is hydrolyzed in a conventional manner, for example, with an alkali such as caustic soda to give the aimed compound.*

Preparation process 6

Aimed compound of the general formula (I) wherein W represents a group of the formula

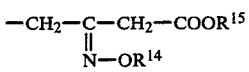

represents a lower alkyl group; and $R^{15}$ represents a hydrogen atom or a lower alkyl group)

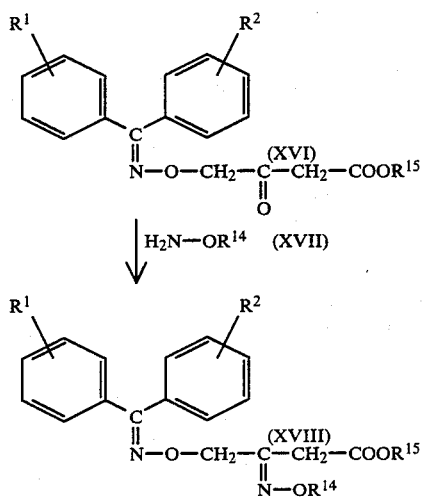

wherein $R^1$, $R^2$, $R^{14}$ and $R^{15}$ are as defined above.

Namely, a compound of the general formula (XVI) is reacted with an amine of the general formula (XVII) to give a compound (XVIII) which is one of the aimed compounds. This reaction may be preferably carried out at a temperature of approximately $-20°$ to $200°$ C. in a solvent such as methanol, ethanol, propanol, benzene, toluene or water.

In order to further illustrate the present invention, and not by way of limitation, typical examples of the compound of the present invention will be given. Each compound will be shown in free form.

4,4-dimethoxybenzophenone O-)3-methoxycarbonyl2-oxopropyl)oxime,
4,4'-dimethoxybenzophenone O-(3-ethoxycarbonyl-2-oxopropyl)oxime,
4,4'-dimethoxybenzophenone O-(3-methoxycarbonyl-2-methoxyiminopropyl)oxime,
4,4'-dimethoxybenzophenone O-(3-ethoxycarbonyl-2-methoxyiminopropyl)oxime,
4,4'-dimethoxybenzophenone O-(3-carboxy-2-methoxyiminopropyl)oxime,
4,4'-dimethoxybenzophenone O-(1-cyano-3-methoxycarbonylpropyl)oxime,
4,4'-dimethoxybenzophenone O-(1-cyano-3-ethoxycarbonylpropyl)oxime,
4,4'-dimethoxybenzophenone O-(1-cyano-3-carboxypropyl)oxime,
4,4'-dimethoxybenzophenone O-(1-cyano-4-methoxycarbonylbutyl)oxime,
4,4'-dimethoxybenzophenone O-(1-cyano-4carboxybutyl)oxime,
4,4'-dimethoxybenozphenone O-{3-[3-allylmercapto-1,2,4-triazolyl)]ethyl}oxime,
4,4'-dimethoxybenzophenone O-{2-[1-(1,2,3,4-tetrzolyl)]ethyl}oxime,
4,4'-dimethoxybenzophenone O-{2-[2-(1,3-dithianyl)]ethyl}oxime,
4,4'-dimethoxybenzophenone O-[2-(1-pyrrolidinyl)-ethyl]oxime,
4,4'-dimethoxybenzophenone O-(2-thiocyanatoethyl)oxime,
4,4'-dimethoxybenzophenone O-(2-mercaptoethyl)oxime,
4,4'-dimethoxybenzophenone O-[2-(1-pyrrolyl)ethyl]oxime,
4,4'-diethoxybenzophenone O-(3-ethoxycarbonyl-2-oxopropyl)oxime,
4,4'-diethoxybenzophenone O-(3-ethoxycarbonyl-2-methoxyiminopropyl)oxime,
4,4'-diethoxybenzophenone O-(3-carboxy-2-methoxyiminopropyl)oxime,
4,4'-diethoxybenzophenone O-(1-cyano-3-ethoxycarbonylpropyl)oxime,
4,4'-diethoxybenzophenone O-(1-cyano-3-carboxypropyl)oxime,
4-methoxybenzophenone O-(3-ethoxycarbonyl-2-oxopropyl)oxime,
4-methoxybenzophenone O-(3-ethoxycarbonyl-2-methoxyiminopropyl)oxime,
4-methoxybenzophenone O-(3-carboxy-2-methoxyiminopropyl)oxime,
4-methoxybenzophenone O-(1-cyano-3-ethoxycarbonylpropyl)oxime, and
4-methoxybenzophenone O-(1-cyano-3-carboxypropyl)oxime.

The diphenyl-methane derivative of the invention, both diphenylene derivative and benzophenone oxime ether derivative, exhibits an excellent effect in the pharmacological point of view. It effectively inhibits the aggulutination of platelets and eventually is useful for a remedy of an antiplatelet and antithrombotic agent. In particular, it is useful for treating and/or preventing cerebrovascular diseases such as transient ischemic attack (TIA), cerebral infarction (thrombus and embolus) and cerebral arteriosclerosis; postoperative thrombus, embolus and blood stream disorders accompanying vascular operation and extracorporeal circulation; chronic arterial obstructions such as Buerger's disease, obstructive arteriosclerosis, peripheral arteriosclerosis, SLE and Raynaud's disease; and ischemic cardial diseases such as stenocardia and myocardial infarction. It is further useful for preventing recurrence of these diseases and for improving prognosis thereof.

The effect of the invention product will be supported by the below given pharmacological tests, first about the diphenylethylene derivative.

TEST EXAMPLE

1. Effect in inhibiting aggulutination of platelets (in vivo)

The blood was collected from a human cubital vein in such a manner as to contain a 3.8% solution of sodium citrate in an amount 1.10 time by volume as much as the blood. Then platelet-rich plasma (PRP) was prepared therefrom according to the method reported by Packham et al. (ct. Packham, M. A., et al, J. Exp. Med., 126, 171–189 (1967)). To 0.2 ml of the obtained PRP, 25 μl portions of solutions of each compound of the present invention (A to E) at various concentrations were added and incubated at 37° C. for three minutes. Then the aggultination of platelets was induced with arachidonic acid, collagen, ADP and PAF. The aggulutination of platelets was evaluated according to the method reported by Mustard et al. (cf. Mustard, J. F., et al., J. Lab. Clin. Med., 64, 548–559 (964) with the use of an aggregometer available from Schenko or Niko Bioscience Co. In other words, this test is carried out to examine the effect of platelet aggregation (in vitro).

Table 1 shows the result.

TABLE 1

| Test Cpd. | Effect of inhibiting collagen aggultination $IC_{50}$ (μM) | Effect of inhibiting arachidonic acid aggultination $IC_{50}$ (μM) | Effect of inhibiting ADP aggultination $IC_{50}$ (μM) | Effect of inhibiting PAF aggultination $IC_{50}$ (μM) |
|---|---|---|---|---|
| Cpd. A (Ex. 1) | 20 | 5 | 5 | 15 |
| Cpd. B (Ex. 2) | 1.4 | 0.9 | 2.0 | 2.5 |
| Cpd. C (Ex. 3) | 0.2 | 0.07 | 0.2 | 1.8 |
| Cpd. D (Ex. 4) | 1.7 | 0.8 | 1.9 | 2.8 |
| Cpd. E (Ex. 5) | 0.15 | 0.06 | 0.2 | 1.3 |

Note:
The compounds A to E as shown above corresponds to the aimed compounds obtained in Examples 1 to 5, respectively.

2. Effect of inhibiting aggulutination of platelets (ex vivo)

The compound A to E, which were typical examples of the compound of the present invention, were orally administered to guinea pigs. After two hours, the blood of each animal was collected from the abdominal aorta thereof under etherization. Then the effect of each compound on the aggultination of platelets induced by collagen (3 μg/ml) and arachidonic acid (50 μM) was examined. Table 2 shows the 50% effective doses determined from the solvent administration ratios. In other words, this test is conducted to examine the effect of platelet aggregation (ex vivo).

TABLE 2

| Test Cpd. | Effect of inhibiting collagen aggultination $ED_{50}$(mg/kg) | Effect of inhibiting arachidonic acid aggultination $ED_{50}$(mg/kg) |
|---|---|---|
| Cpd. A (Ex. 1) | 100 | 100 |
| Cpd. B (Ex. 2) | 20 | 20 |
| Cpd. C (Ex. 3) | 0.05 | 0.03 |
| Cpd. D (Ex. 4) | 0.05 | 0.03 |
| Cpd. E (Ex. 5) | 1 | 0.3 |
| Ticlopidine | ≦200 | 150 |

3. Acute toxicity

The acute toxicities of the compounds A to E, which were typical examples of the compound of the present invention, were examined by administrating these compounds to male Wistar rats of 300 to 400 g in body weight. As a result, the $LD_{50}$ of each compound was higher than 500 mg per kg.

The effect of the invention will be supported also in view of the benzophenone oxime either derivatives by the below given test data.

The test compounds L to R correspond to the products of Examples 11 to 17, respectively.

The tests were conducted in the same way as shown before from the diphenylethylene derivative. Results for inhibition of aggulutination are shown in Table 3 for the in-vitro test and in Table for the ex-vivo test. The acute toxicity test provided the same results as obtained with the diphenylethylene derivative.

TABLE 3

| Test Cpd. | Effect of inhibiting collagen aggultination $IC_{50}$ (μM) | Effect of inhibiting arachidonic acid aggultination $IC_{50}$ (μM) | Effect of inhibiting ADP aggultination $IC_{50}$ (μM) | Effect of inhibiting PAF aggultination $IC_{50}$ (μM) |
|---|---|---|---|---|
| Cpd. L (Ex. 11) | 0.5 | 0.1 | 0.8 | 1.2 |
| Cdp. M (Ex. 12) | 14.0 | 12.5 | 13.2 | 20.0 |
| Cpd. N (Ex. 13) | 2.8 | 0.7 | 5.0 | 4.1 |
| Cpd. O (Ex. 14) | 14.0 | 7.0 | 20.0 | 14.5 |
| Cpd. P (Ex. 15) | 1.1 | 0.4 | 2.7 | 1.5 |
| Cpd. Q (Ex. 16) | 36.0 | 12.0 | 35.0 | 37.0 |
| Cpd. R (Ex. 17) | 80.0 | 50.0 | 85.0 | 79.0 |

TABLE 4

| Test Cpd. | Effect of inhibiting collagen aggultination $ED_{50}$(mg/kg) | Effect of inhibiting arachidonic acid aggultination $ED_{50}$(mg/kg) |
|---|---|---|
| Cpd. L (Ex. 11) | 30 | 30 |
| Cpd. M (Ex. 12) | 55 | 55 |
| Cpd. N (Ex. 13) | 1.3 | 0.3 |
| Cpd. O (Ex. 14) | 1.0 | 0.3 |
| Cpd. P (Ex. 15) | 1.1 | 0.3 |

TABLE 4-continued

| Test Cpd. | Effect of inhibiting collagen aggultination ED$_{50}$(mg/kg) | Effect of inhibiting arachidonic acid aggultination ED$_{50}$(mg/kg) |
| --- | --- | --- |
| Cpd. Q (Ex. 16) | 88 | 50 |
| Cpd. R (Ex. 17) | ≦100 | ≦100 |
| Ticlopidine | ≦200 | 150 |

When the compound of the present invention is used as an antiplatelet and antithrombotic agent, it may be orally or parenterally, for example, intramuscularly, subcutaneously or intravenously administered. The dose thereof may vary depending on, for example, the disease, the condition and the age of each patient. Unless particularly limited, it may be administered in a dose of 0.1 to 300 mg, preferably 0.1 to 60 mg, particularly preferably 0.3 to 30 mg, further particularly preferably 0.6 to 10 mg to an adult per day.

The compound of the present invention may be formulated into, for example, tablets, granules, powders, capsules, injections or suppositories in conventional manner know in the art.

When it is to be formulated into solid preparations for oral administration, excipients and, if required, other additives such as binders, disintegrants, lubricants, colorants and corrigents are added to the base and the obtained mixture is then formulated into, for example, tablets, coated tablets, granules, powders or capsules in conventional manners.

Examples of the excipients are lactose, corn starch, white sugar, glucose, sorbitol and crystalline cellulose. Examples of the binders are polyvinyl alcohol, polyvinyl ether, ethylcellulose, methylcellulose, gum arabic, tragacanth, gelatin, sheller, hydroxypropylcellulose, hydroxypropylstarch and polyvinylpyrrolidone. Examples of the disintegrants are starch, agar, powdery gelatin, crystalline cellulose, calcium carbonate, calcium hydrogencarbonate, calcium citrate, dextrin and pectin. Examples of the lubricants are magnesium stearate, talc, polyethylene glycol, silica and hardened vegetable oils. Examples of the colorants are those approved as additives for drugs. Examples of the corrigents are cocoa powder, methol, aromatic acids, peppermint oil, Borneo camphor and cinnamon powder. These tablets and granules may be, as a matter of course, coated with, for example, sugar or gelatin if required.

When an injection is to be prepared, various additives such as pH adjustors, buffers, stabilizers and preservatives are added to the base of the obtained mixture is formulated into an injection for subcutaneous, intramuscular or intravenous administration.

The further illustrate the present invention, and not by way of limitation, the following Examples will be given.

EXAMPLE 1

N-Benzyl-3,3-bis(4-methoxyphenyl)acrylamide 2.84 g (0.01 M) of 3,3-bis(4-methoxyphenyl)acrylic acid was dissolved in 10 ml of dimethylformamide. To the obtained solution, 1.2 g (0.012 M) of triethylamine and 1.2 g of ethyl chlorocarbonate were added under icecooling. After on hour, 1.2 g of benzylamine was added thereto and the mixture was stirred at room temperature for one hour. After the completion of the reaction, the reaction mixture was dissolved in 50 ml of ethyl acetate, washed with 10% hydrochloric acid, a saturated aqueous solution of NaHCO$_3$ and a saline solution successively and dried over magnesium sulfate followed by purifying by silica gel column chromateg-raphy. Thus 3.3 g of the title compound having the following physicochemical properties was obtained.
m.p.: 99°–100° C.
NMR (CDCl$_3$)δ: 6.7–7.3(13H), 6.3(1H), 5.5(1H), 4.3(2H) and 3.8(6H).

EXAMPLE 2

N-[3,3-Bis(4-methoxyphenyl)allyl]benzensulfonamide.

2.69 g of 3,3-bis-(4-methoxyphenyl)allylamine was dissolved in 5 ml of pyridine. To the obtained solution, 1.9 g of benzenesulfonyl chloride was added under icecooling and the mixture was stirred for five hours. After the completion of the reaction, the reaction mixture was dissolved in ethyl acetate and washed with 5% hydrochloric acid and a saturated saline solution successively. The crude product thus obtained was purified by silica gel chromatography in a conventional manner. Thus 3.6 g of the title compound was obtained in the form of a colorless oily product.
NMR (CDCl$_3$)δ: 7.8(2H), 7.5(3H), 6.7–7.1(8H), 5.8(1H), 4.4(1H), 3.8(6H), 3.7(2).

EXAMPLE 3

Ethyl 4-cyano-5,5-bis(4-methoxyphenyl)-4-pentenoate 2.42 g (0.01 M) of 4,4′-dimethoxybenzophenone, 1 g of zinc and 2.1 g or trimethyl borate were suspended in 15 ml of tetrahydrofuran. To the obtained suspension, 2.2 g of ethyl 4-bromo-4-cyanobutyrate and a catalytic amount of iodine wee added and the mixture was allowed to react to room temperature for five hours. After the completion of the reaction, 10 ml of a saturated aqueous solution of ammonium chloride was added thereto and the mixture was stirred for one hour. After filtering the zinc off, the filtrate was extracted with ethyl acetate. The obtained crude product was purified by silica gel chromatography to give 1.5 g of crystals. The crystals were dissolved in 10 ml of benzene and 1 ml of thionyl chloride was added to the obtained solution. After stirring at room temperature for one hour, the reaction mixture was concentrated in vacuo and dispersed into ice/water. Then it was extracted with benzene, washed with water and concentrated. Thus 1.3 g of the title compound was obtained in the form of a colorless oily product.
NMR (CDCl$_3$)δ: 6.7–7.3(8H), 4.1(2H), 2.7(4H) and 1.3(3H).

EXAMPLE 4

4-Cyano-5,5-bis(4-methoxyphenyl)4-pentenoic acid 3.6 g or ethyl 4-cyano-5,5-bis(4-methoxyphenyl)-4-pentenoate was dissolved in 10 ml of dioxane and 3 ml of a 5N aqueous solution of NaOH was added thereto. The obtained mixture was stirred at 60° C. for five hours. After the completion of the reaction, the reaction mixture was acidified and extracted with ethyl acetate. Thus 3.2 g of the title compound having the following physicochemical properties was obtained. This product could be further purified by recrystallizing form ethyl acetate/hexane.
m.p.: 124°–125° C.

NMR (CDCl$_3$)δ: 9.5(1H), 6.8–7.4(8H), 3.8(6H), 2.7(4H).

EXAMPLE 5

Methyl 5-cyano-6,6-bis(4-methoxyphenyl)-5-hexenoate

The procedure of Example 3 was followed except that the ethyl 4-bromo-4-cyanobutyrate was replaced by 2.2 g of methyl 5-bromo-5-cyanopentanoate. Thus the title compound having the following physicochemical properties was obtained.

NMR (CDCl$_3$)δ: 6.7–7.3(8H), 3.8(6H), 3.6(3H) and 1.8–2.6(6H).

EXAMPLES 6 TO 13

6. N-phenyl-3,3-bis(4-methoxyphenyl)acrylamide
7. N-(3-pyridyl)-3,3-bis(4-methoxyphenyl)acrylamide
8. N-(4-pyridyl)-3,3-bis(4-methoxyphenyl)acrylamide
9. N-(2-chlorobenzyl)-3,3,-bis(4-methoxyphenyl)acrylamide
10. N-(3-pyridyl)methyl-3,3-bis(4-methoxyphenyl)acrylamide
11. N-benzyl-N-methyl-3,3-bis(4-methoxyphenyl)acrylamide
12. N-benzyl-N-isopropyl-3,3-bis(4-methoxyphenyl)acrylamide
13. N-(2-(N,N-dimethylamino)ethyl)-N-(2-)3,4-dimethoxyphenyl)ethyl)-3,3-bis(4-methoxyphenyl)acrylamide Each of the above listed compounds was obtained in the same way as shown in Example 1, except benzylamine was replaced by the respective, below listed compounds.

6. aniline, 7. 3-aminopyridine, 8. 4-aminopyridine, 9. 2-chlorobenzylamine, 10. 3-aminomethylpyridine, 11. N-methylbenzylamine, 12, N-isopropylbenzylamine, and 13. N,N-dimethyl-N'-(2-(3,4-dimethoxyphenyl)ethyl)ethylenendiamine.

EXAMPLE 14 ethyl 3,3-bis(4-methoxyphenyl)-N-phenyl-acrylic imide

One gram (2.8 mmol) of the amide obtained in Example 6 was reacted with 10 ml of phosphorus oxychloride at 60° C. for 2 hours. The product mixture was condensed and mixed with 50 ml of chloroform, 5 ml or ethanol and 5 ml of N,N-dimethylaniline, followed by further reaction at 60° C. for 2 hours, obtain 0.2 g of the above named compound.

EXAMPLE 15

3,3-bis(4-methoxyphenyl)-N,N'-diphenylacrylic amidine

This was obtained by reaction between 1 g of the amide obtained in Example 6 and 0.3 ml of aniline with 0.3 ml of phosphorus oxychloride in 20 ml of toluene for 3 hours while refluxed. The amount was 80 mg.

EXAMPLE 16 allyl 3,3-bis(4-methoxyphenyl)-N-phenyl-acrylic thioimide

One gram of the amide obtained in Example 6 was reacted with 1.2 g of phosphorus pentasulfide in 50 ml of benzene at 50° C. for 1 hour. The product mixture was condensed and dissolved in chloroform, followed by washing with water. 0.6 g of the thioamide was obtained from the product mixture with the chromatography using silicagel. 0.6 g (1.6 mmol) of the thioamide was reacted with 2.0 g (16 mmol) of ally bromide with 0.5 g of potassium carbonate in 50 ml of tetrafurane at the room temperature over one night. The reaction product mixture was condensed and dissolved in chloroform, followed by washing with water. 0.45 g of the above intended compound was obtained with the chromatography of silicagel.

EXAMPLE 17 ethyl 3-methoxyimino-5,5-bis(4-methoxyphenyl)-4-pentenoate 4.0 g (11.3 mmol) of ethyl 3-oxy-5,5-bis(4-methoxyphenyl)-4-pentenoate was reacted with 2.0 g (24.0 mmol) of hydrochloric acid salt of methoxyamine in 50 ml of pyridine at 60° C. for 2 hours. 3.2 g of the above intended compound was obtained.

EXAMPLE 18

3-methoxyimino-5,5-bis(4-methoxyphenyl)-4-pentenoic acid 2.0 g of the above intended compound was obtained by the same reaction as shown in Example 4 from the ester obtained in Example 17.

EXAMPLE 19

N-(3,3-bis(4-methoxyphenyl)allyl)-methanesulfonic amide

EXAMPLE 20

N-(3,3-bis(4-methoxyphenyl)ally)-4-carboxybenzenesulfonic amide

These were obtained by the same reaction as shown in Example 2, except that methanesulfonic chloride and 4-(chlorosulfonyl)benzoic acid were respectively used instead of benzenesulfonic chloride.

EXAMPLE 21

4-cyano-5,5-bis(4-ethoxyphenyl)-4-pentenoic acid

Example 3 was followed except for using 4,4'-diethoxybenzophenone and tetrahydrofurane as a solvent. The product mixture was dehydrated with thionyl chloride and hydrolyzed in the same way as shown in Example 4.

EXAMPLE 22

4-cyano-5-(4-hydroxyphenyl)-(Z)-5-(4-methoxyphenyl)-4-pentenoic acid and the (E) compound thereof Example 3 was followed except for using 4-methoxy-4'-methoxymethoxybenzophenone. The product mixture was treated with hydrochloric acid and hydrolyzed in the same way as shown in Example 4. The elution of the product mixture with a mixture of methanol and chloroform at a ration of 5:95 in the chromatography using silicagel provided the (Z) compound. The elution with the mixture at a ration of 10:90 provided the (E) compound.

EXAMPLE 23

4-cyano-5-(4-hydroxyphenyl)-(Z)-5-(4-ethoxyphenyl)-4-pentenoic acid 4-pentenoic acid and the (E) compound thereof Example 22 was followed except for using 4-ethoxy-4'-methoxymethoxybenzophenone.

EXAMPLE 24

4-cyano-5,5-bis(4-hydroxyphenyl)-4-pentenoic acid

EXAMPLE 25

4-cyano-2-methyl-5,5-bis(4-methoxyphenyl)-4-pentenoic acid

Example 22 was followed except for using 4,4'-dimethoxymethoxybenzophenone and 4,4'-dimethoxybenzophenonone. The hydrolysis product was the above intended compound.

EXAMPLE 26

4-carboxy-5,5-bis(4-methoxyphenyl)-4-pentenoic acid

Example 3 was followed except that diethyl 2-bromoglutarate was used for ethyl 4-bromo-4-cyanobutyrate and the hydrolysis was conducted in the same way as shown in Example 4.

EXAMPLE 27

4-carbamoyl-5,5-bis(4-methoxyphenyl)-4-pentenoic acid

Two grams of the acid obtained in Example 4 was heated with 10 ml of a 5N aqueous solution of NaOH in 50 ml of ethylene glycol at 150° C. for 12 hours. The product mixture was acidified with hydrochloric acid and extracted with ethyl acetate. The extract was treated with the chromatography of silicagel to obtain 0.5 g of the above intended compound.

EXAMPLE 28

5-cyano-6,6-bis(4-methoxyphenyl)-5-hexenoic acid 260 mg of the ester obtained in Example 5 was treated in the same way as shown in Example 4 to obtain 250 mg of the above intended compound.

The data of the NMR analysis about the compounds obtained in Examples 6 to 28 is listed below. The analysis was conducted with CDCl$_3$, δ

| examples | analysis |
|---|---|
| 6 | 6.8–7.4(14H), 6.4(1H), 3.9(6H) |
| 7 | 7.9–8.4(3H), 6.8–7.4(10H), 6.4(1H), 3.8(6H) |
| 8 | 8.3(3H), 6.7–7.3(10H), 6.3(1H), 3.8(6H) |
| 9 | 7.0–7.3(8H), 6.7–6.9(4H), 6.3(1H), 5.7(1H), 4.4(2H), 3.8(6H) |
| 10 | 8.5(1H), 8.3(1H), 7.0–7.5(6H), 6.8(4H), 6.3(1H), 5.6(1H), 4.3(2H), 3.8(6H) |
| 11 | 6.7–7.4(13H), 6.3(1H), 4.5(2H), 3.8(6H), 2.7(3H) |
| 12 | 6.6–7.5(13H), 6.4(1H), 4.8(1H), 4.5(2H), 3.8(6H), 1.0(6H) |
| 13 | 6.6–7.4(11H), 6.2(1H), 3.8(12H), 3.2–3.7(4H), 2.1–2.8(10H) |
| 14 | 6.5–7.6(13H), 5.9(1H), 4.0(2H), 3.8(6H), 0.9(3H) |
| 15 | 6.6–7.4(19H), 6.1(1H), 3.8(6H) |
| 16 | 6.5–7.3(13H), 6.2(1H), 5.8(1H), 5.1(2H), 3.5–3.8(8H) |
| 17 | 6.7–7.3(8H), 6.6(1H), 4.0(2H), 3.9(3H), 3.8(6H), 2.9(2H), 1.2(3H) |
| 18 | 10.0(1H), 6.7–7.3(9H), 3.9(3H), 3.8(6H), 2.9(2H) |
| 19 | 6.6–7.4(8H), 5.9(1H), 4.4(1H), 3.8(8H), 2.9(3H) |
| 20 | 10.0(1H), 7.6–8.2(4H), 6.5–7.1(8H), 5.7(1H), 4.4(1H), 3.4–3.9(8H) |
| 21 | 9.5(1H), 6.6–7.2(8H), 4.0(4H), 2.6(4H), 1.4(6H) |
| 22 | 8.0–9.5(2H), 7.1–7.5(2H), 6.7–7.0(6H), 3.8(3H), 2.7(4H) |
| 23 | 7.5–9.5(2H), 7.0–7.3(2H), 6.6–6.9(6H), 4.0(2H), 2.6(4H), 1.4(3H) |
| 24 | 8.5–10.0(3H), 6.7–7.4(8H), 2.6(4H) |
| 25 | 9.0(1H), 7.1–7.3(2H), 6.6–7.0(6H), 3.8(6H), 2.3–3.1(3H), 1.2(3H) |
| 26 | 8.0–9.5(2H), 6.7–7.4(8H), 3.8(6H), 2.7(4H) |
| 27 | 8.2(1H), 6.6–7.2(10H), 3.7(6H), 2.3(4H) |
| 28 | 8.0–9.0(1H), 7.1–7.3(2H), 6.7–7.0(6H), 3.8(6H), 2.2–2.5(4H), 1.8–2.2(2H) |

The above shown examples relate to the first group of the invention. The second embodiment will be illustrated below.

EXAMPLE 29

4,4'-dimethoxybenzophenone-O-(3-ethoxycarbonyl-2-oxopropyl)oxime (1) Synthesis of 4,4'-dimethoxybenzophenone oxime 242 g (1 mole) of 4,4'-dimethoxybenzophenone was suspended in 2,000 ml of ethanol and 210 g (3 mole) of hydroxylamine hydrochloride and 300 ml (3 mole) of a 10 N aqueous solution of NaOH were thereto. Then the obtained mixture was heated under reflux. After two or three hours, the ethanol was distilled off in vacuo and then a saline solution was added thereto followed by extracting with chloroform. The chloroform phase was washed with water and dried over magnesium sulfate. After distilling the chloroform off, the residue was recystallized from ethanol. Thus 240 g of the title compound was obtained in the form of colorless needles.

m.p.: 131° to 132° C.

NMR (CDCl$_3$)δ: 9.60 (b-s, 1H), 7.50 (m, 8H), 3.83 (s, 3H) 3.80 (s, 3H).

(2) Synthesis of 4,4'-dimethoxybenzophenone O-(3-ethoxycarbonyl-2-oxopropyl)oxime 2.57 g (0.01 mol) of the 4,4'-dimethoxybenzophenone oxime as obtained in (1) was dissolved in 5 ml of dimethylformamide and 1.2 g of potassium tert-butoxide was added thereto under ice cooling. The resulting mixture was stirred for ten minutes. Then 1.8 g of ethyl 4-chloroacetoacetate was added thereto and the obtained mixture was stirred at room temperature. After two hours, the reaction mixture was poured into diluted hydrochloric acid and extracted with ethanol. The crude product thus obtained was purified by silica gel chromatography to give 3.1 g of the title compound.

NMR (CDCl$_3$)δ: 6.7–7.4(8H), 4.6(2H) 3.9–4.2(2H) 3.8(6H) 3.5(2H), 1.2(3H).

EXAMPLE 30

4,4'-Dimethoxybenzophenone O-(3-ethoxycarbonyl-2-methoxyiminopropyl)oxime 3.85 g of the 4,4'-dimethoxybenzophenone O-(3-ethoxycarbonyl-2- oxopropyl)oxime as obtained in Example 1 was dissolved in 5 ml of pyridine and 1 g of methoxylamine hydrochloride was added thereto. Then the obtained mixture was stirred at room temperature. After two hours, the reaction mixture was poured into ethyl acetate, washed with diluted hydrochloric acid and then with a saturated saline solution and purified by silica gel chromatography. Thus 4 g of the title compound was obtained in the form of a colorless oily product.

NMR (CDCl₃)δ: 6.7-7.4 (8H), 5.0, 4.7 (2H) 3.8-4.2 (2H) 3.8 (9) 3.3, 3.4 (2H) 1.0-1.2(3H).

EXAMPLE 31

4,4'-Dimethoxybenzophenone O-(3-carboxy-2-methoxyiminopropyl)oxime 4.14 g of the 4,4'-dimethoxybenzophenone O-(3-ethoxycarbonyl-2-methoxyiminopropyl)oxime as obtained in Example 30 was dissolved in 20 ml of methanol and 3 ml of a 5 N aqueous solution of caustic soda was added thereto. The obtained mixture was stirred at room temperature for five hours. After the completion of the reaction, the reaction mixture was acidified with diluted hydrochloric acid and extracted with ethyl acetate. Thus 3.8 g of the title compound was obtained in the form of a colorless oily product.

NMR (CDCl₃)δ: 9.50 (1H), 6.8-7.5(8), 5.0, 6.8(2H), 3.8-3.9(9H), 3.5, 3.3(2H).

EXAMPLE 32

4,4'Dimethoxybenzophenone O-(1-cyano-3-ethoxycarbonylpropyl)oxime

The procedure of Example 29 was followed except that the ethyl 4-chloroacetoacetate was replaced by 2.2 g of ethyl 4-bromo-4-cyanobutyrate. Thus 3.6 g of the title compound having the following properties was obtained.

NMR (CDCl₃)δ: 6.8-7.5 (8H), 5.0 (1H), 4.0-4.3(2H), 3.8(6H), 2.2-2.6 (4H), 1.2 (3).

EXAMPLE 33

4,4'-Dimethoxybenzophenone O-(1-cyano-3-carboxypropyl)oxime 3.96 g of the 4,4'-dimethoxybenzophenone O-(1-cyano-3-ethoxycarbonylpropyl)oxime was dissolved in 20 ml of dioxane and 3 mil of a 5 N aqueous solution of caustic soda was added thereto. Then the mixture was allowed to react at 20 C. for five hours. After the completion of the reaction, the reaction mixture was acidified and extracted with ethyl acetate. Thus 3.6 g of the title compound was obtained in the form of a colorless oily product.

NMR (CDCl₃)δ: 6.7-7.5 (8H), 5.0 (1H) 3.8 (6H) 2.1-2.7 (4H).

EXAMPLE 34

4,4'-Dimethoxybenzophenone O-(1-cyano-4-methoxycarbonylbutyl)oxime

The procedure of Example 29 was followed except that the ethyl 4-chloroacetoacetate was replaced by 2.2 g or methyl 5-bromo-5-cyanopentanoate. Thus 3.7 g of the title compound of the following properties was obtained.

NMR (CDCl₃)δ: 6.8-7.6 (8H), 4.9(1), 3.8 (6H), 3.6(3H), 2.4(2H), 1.6-2.2 (4H).

EXAMPLE 35

4,4'-Dimethoxybenzophenone O-(1-cyano-4-carboxybutyl)oxime

According to the procedure of Example 33, the title compound of the following properties was obtained.

NMR (CDCl₃)δ: 6.8-7.6 (8H), 4.9(1), 3.8 (6H), 2.4(2), 1.6-2.2(4H).

What is claimed is:

1. A substituted benzophenone oxime ether derivative having the formula

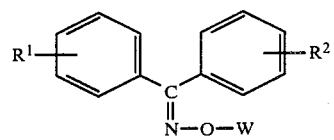

wherein each of $R^1$ and $R^2$ is hydrogen, hydroxyl or lower alkoxy; W is (1)

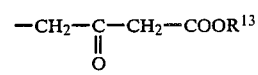

in which $R^{13}$ is hydrogen or lower alkyl, (2)

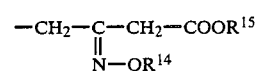

in which $R^{15}$ is hydrogen or lower alkyl and $R^{14}$ is lower alkyl, (3)

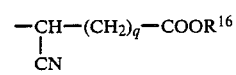

in which $R^{16}$ is hydrogen or lower alkyl and q is an integer of 1, 2 or 3, or (4) —(CH₂)ₚ—Z in which —Z is —SH or —SCN, and p is an integer of 1 or 2, or pharmacologically acceptable salt thereof.

2. A substituted benzophenone oxime ether derivative as set forth in claim 1, wherein both of $R^1$ and Rhu 2 are lower alkoxy groups.

3. A substituted benzophenone oxime ether derivative as set forth in claim 1, wherein both of $R^1$ and $R^2$ are methoxy groups.

4. A substituted benzophenone oxime ether derivative as set forth in claim 1, wherein both of $R^1$ and $R^2$ are lower alkoxy groups and W is a group of the formula

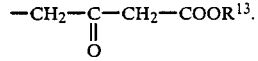

5. A substituted benzophenone oxime ether derivative as set forth in claim 1 wherein both of $R^1$ and $R^2$ are lower alkoxy groups and W is a group of the formula

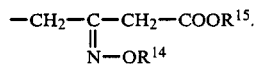

6. A substituted benzophenone oxime ether derivative as set forth in claim 1 wherein both of $R^1$ and $R^2$ are lower alkoxy groups and W is a group of the formula

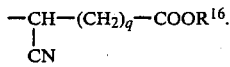

7. A substituted benzophenone oxime ether derivative as set forth in claim 1 wherein both of $R^1$ and $R^2$ are lower alkoxy groups and W is a group of the formula $-(CH_2)_p-Z$.

8. A substituted benzophenone oxime ether derivative as set forth in claim 1 wherein both of $R^1$ and $R^2$ are methoxy groups and W is a group of the formula

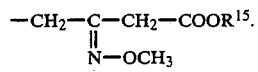

9. A substituted benzophenone oxime ether derivative as set forth in claim 1 wherein both of $R^1$ and $R^2$ are methoxy groups and W is a group of the formula

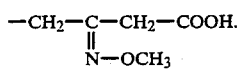

10. A substituted benzophenone oxime ether derivative as set forth in claim 1 wherein both of $R^1$ and $R^2$ are methoxy groups and W is a group of the formula

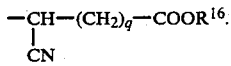

11. A substituted benzophenone oxime ether derivative as set forth in claim 1 wherein both of $R^1$ and $R^2$ are methoxy groups and W is a group of the formula

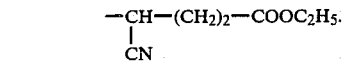

12. A substituted benzophenone oxime ether derivative as set forth in claim 1 wherein both of $R^1$ and $R^2$ are methoxy groups and W is a group of the formula

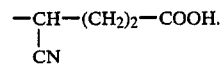

13. A compound as claimed in claimed 1, namely, 4,4'-dimethoxybenzophenone O-(3ethoxycarbonyl-2-oxopropyl)oxime.

14. A compound as claimed in claim 1, namely, 4,4'-dimethoxybenzophenone O-(3-ethoxycarbonyl-2-methoxyiminopropyl)oxime.

15. A compound as claimed in claim 1, namely, 4,4'-dimethoxybenzophenone O-(3-carboxy-2-methoxyiminopropyl)oxime.

16. A compound as claimed in claim 1, namely, 4,4'-dimethoxybenzophenone O-(1-cyano-4-methoxycarbonylbutyl)oxime.

17. A compound as claimed in claim 1, namely, 4,4'-dimethoxybenzophenone O-(1-cyano-4-carboxybutyl)oxime.

18. A pharmaceutical composition which comprises a pharmacologically effective amount of the substituted benzophenone oxime ether derivative as defined in claim 1 or a pharmacologically acceptable salt thereof and a pharmacologically acceptable carrier.

19. A method for treating a patient having a disease caused by aggregation of platelets or formation of thrombus which comprises administering to the patient a therapeutically effective amount of a pharmaceutical composition as claim in claim 18.

* * * * *

UNITED STATES PATENT AND TRADEMARK OFFICE
CERTIFICATE OF CORRECTION

PATENT NO. : 4 954 523

DATED : September 4, 1990

INVENTOR(S) : Youji YAMAGISHI et al

It is certified that error appears in the above-identified patent and that said Letters Patent is hereby corrected as shown below:

Column 24, line 44; change "Rhu" to ---$R_2$---.

line 45; delete "2".

Signed and Sealed this

Twenty-first Day of April, 1992

Attest:

HARRY F. MANBECK, JR.

*Attesting Officer*      *Commissioner of Patents and Trademarks*